United States Patent
Yamamoto (10) Patent No.: US 9,655,760 B2
(45) Date of Patent: May 23, 2017

(54) KNEE SUPPORT

(75) Inventor: Naotaka Yamamoto, Chofu (JP)

(73) Assignee: NIPPON SIGMAX CO., LTD., Tokyo (JP)

( * ) Notice: Subject to any disclaimer, the term of this patent is extended or adjusted under 35 U.S.C. 154(b) by 137 days.

(21) Appl. No.: 14/236,238

(22) PCT Filed: Jun. 26, 2012

(86) PCT No.: PCT/JP2012/066214
§ 371 (c)(1),
(2), (4) Date: Jan. 30, 2014

(87) PCT Pub. No.: WO2013/021743
PCT Pub. Date: Feb. 14, 2013

(65) Prior Publication Data
US 2014/0243723 A1    Aug. 28, 2014

(30) Foreign Application Priority Data
Aug. 9, 2011    (JP) .................. 2011-174046

(51) Int. Cl.
*A61F 5/00*    (2006.01)
*A61F 5/01*    (2006.01)
*A61F 13/06*   (2006.01)

(52) U.S. Cl.
CPC .......... *A61F 5/0123* (2013.01); *A61F 5/0106* (2013.01); *A61F 13/061* (2013.01); *A61F 2005/0176* (2013.01)

(58) Field of Classification Search
CPC .... A61F 5/0106; A61F 5/0109; A61F 5/0111; A61F 5/0123; A61F 5/0125;
(Continued)

(56) References Cited

U.S. PATENT DOCUMENTS 3,046,981 A * 7/1962 Biggs, Jr. ............. A61F 5/0109
602/26
4,240,414 A   12/1980 Theisler
(Continued)

FOREIGN PATENT DOCUMENTS

| JP | 2003 88544 | 3/2003 |
|---|---|---|
| JP | 2006 6375 | 1/2006 |
| JP | 2006 223845 | 8/2006 |

OTHER PUBLICATIONS

International Search Report Issued Jul. 31, 2012 in PCT/JP12/066214 Filed Jun. 26, 2012.
(Continued)

*Primary Examiner* — Michael Brown
(74) *Attorney, Agent, or Firm* — Oblon, McClelland, Maier & Neustadt, L.L.P.

(57) ABSTRACT

Provided is a knee support capable of correcting/alleviating an inner rotation or outer rotation of a knee joint.
A knee support comprising a support main body for covering a knee joint, and a strap to be wound around and attached on an outer surface of the support main body helically while being pulled in the direction opposite to an inner rotation direction of the joint, wherein a projection to be contacted with an inner side of a shinbone below the knee when wearing is provided on the inner surface of the support main body or the inner surface of the strap.

4 Claims, 5 Drawing Sheets

(58) Field of Classification Search
CPC ............ A61F 13/061; A61F 2005/0176; A61F 2005/0167; A61F 2005/0174; A61F 2005/0179; A61F 13/062; A61H 1/024; A63B 2071/027; A63B 2071/1258; A63B 2071/1266; A63B 2071/1283; A63B 2208/12; A63B 71/12; A63B 71/1225; Y10S 2/91; Y10S 2/911; B29C 2043/464; B29C 43/222; B29C 47/003; B29C 47/0033; B29C 47/00
USPC ........................ 602/16, 23–28; 128/882; 2/16
See application file for complete search history.

(56) References Cited

U.S. PATENT DOCUMENTS

| | | | |
|---|---|---|---|
| 4,370,978 A | | 2/1983 | Palumbo |
| 4,445,505 A | | 5/1984 | Labour et al. |
| 4,532,921 A | * | 8/1985 | von Torklus et al. .......... 602/26 |
| 4,693,241 A | | 9/1987 | Trznadel |
| 4,756,026 A | * | 7/1988 | Pierce, Jr. ............................ 2/16 |
| 5,797,864 A | * | 8/1998 | Taylor ............................. 602/26 |

OTHER PUBLICATIONS

Written Opinion was Issued Jul. 31, 2012 in PCT/JP12/066214 Filed Jun. 26, 2012.
European Search Report dated Jul. 22, 2015 for Application No. 12821470.7.

* cited by examiner

KNEE SUPPORT

FIELD OF THE INVENTION

The present invention relates to a knee support capable of correcting or alleviating inner rotation or outer rotation of a knee joint.

BACKGROUND OF THE INVENTION

Various forms of knee support have conventionally been reported, and all of them are for obtaining an appropriate supporting and fixing power and facilitating smooth movement of the joint by appropriately combining members with different expansion and contraction ratios or providing a pad thereto (see Patent Document 1).

Therefore, in some conventional knee supports, an inner rotation and outer rotation of a knee joint may not be actually restrained or corrected.

CITATION LIST

Patent Document

Patent Document 1: JP 2003-88544 A

SUMMARY OF THE INVENTION

Problem to be Solved by the Invention

The present invention has been achieved in view of the conventional situation as mentioned above, and its objective is to provide a knee support capable of restraining or correcting an inner rotation or an outer rotation of a knee joint.

Means for Solving Problem

As a result of various studies for solving the problem mentioned above, the present inventor found that the inner rotation and the outer rotation can certainly be restrained by inhibiting displacement movement of the support itself by using in combination a support main body having a projection to be engaged with bones and muscles below the knee joint and a strap to be fixed by being wound around helically while being pulled to the direction opposite to the inner rotation or outer rotation direction of the joint, although the inner rotation and the outer rotation of the knee joint cannot be restrained merely by placing a strap on the worn knee support as the support itself is displaced in the strap pulling direction. Based on such findings, the present inventor has completed the present invention.

That is, the present invention has solved the above-mentioned problem by a knee support comprising a support main body for covering a knee joint, and a strap to be wound around and attached on an outer surface of the support main body helically while being pulled in the direction opposite to an inner rotation direction of the joint, wherein a projection to be contacted with an inner side of a shinbone below the knee when wearing is provided on the inner surface of the support main body or the inner surface of the strap.

In addition, the present invention has solved the above-mentioned problem by a knee support comprising a support main body for covering a knee joint, and a strap to be wound around and attached on an outer surface of the support main body helically while being pulled in the direction opposite to an inner rotation direction of the joint, wherein a projection to be contacted with the vicinity of a distal adhesion of a semimembranous muscle below the knee when wearing is provided on the inner surface of the support main body or the inner surface of the strap.

Furthermore, the present invention has solved the above-mentioned problem by a knee support comprising a support main body for covering a knee joint, and a strap to be wound around and attached on an outer surface of the support main body helically while being pulled in the direction opposite to an outer rotation direction of the joint, wherein a projection to be contacted with an outer surface of a shinbone below the knee when wearing is provided on the inner surface of the support main body or the inner surface of the strap.

Moreover, the present invention has solved the above-mentioned problem by a knee support comprising a support main body for covering a knee joint, and a strap to be wound around and attached on an outer surface of the support main body helically while being pulled in the direction opposite to an outer rotation direction of the joint, wherein a projection to be contacted with the vicinity of a distal adhesion of a biceps femoris muscle below the knee when wearing is provided on the inner surface of the support main body or the inner surface of the strap.

Effects of the Invention

According to the present invention, the projection provided in the support main body or the strap is, when wearing, engaged with the shinbone, the distal adhesion of the semi-membranous muscle or the distal adhesion of the biceps femoris muscle along the strap pulling direction at the contact region so as to serve as a stopper for the support main body, even if the strap is wound around and fixed while being pulled in the direction opposite to the inner rotation or outer rotation direction. Therefore, the support main body is not displaced in the strap pulling direction of the strap, thereby further certainly restraining the inner rotation or the outer rotation. As a result of that, the inner rotation or the outer rotation of the knee joint is effectively corrected or alleviated by wearing the knee support of the present invention.

DETAILED DESCRIPTION OF THE INVENTION

Hereafter, embodiments of the present invention will be explained with reference to the drawings.

Figure 1:
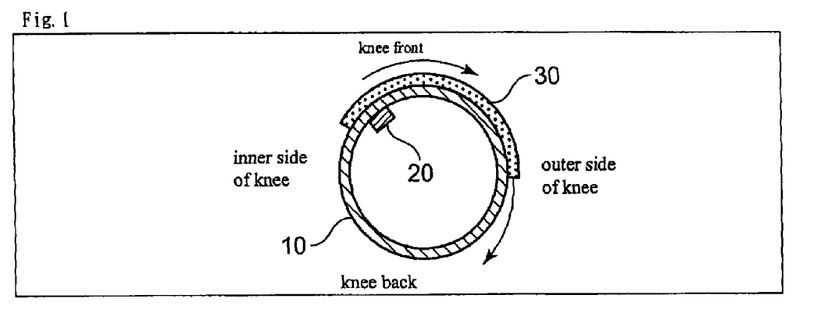
FIG. 1 is a schematic cross-sectional explanatory drawing for showing a first embodiment of a knee support of the present invention.

FIG. 1 is a schematic cross-sectional explanatory drawing for showing a support for restraining/correcting an inner rotation of the right leg according to a first embodiment of the present invention.

In FIG. 1, 10 is a support main body. Its form is not limited as long as it can cover the knee joint. It may either be of a close type, an open type or a semi close type. Moreover, its material may be of any kind.

Figure 9:
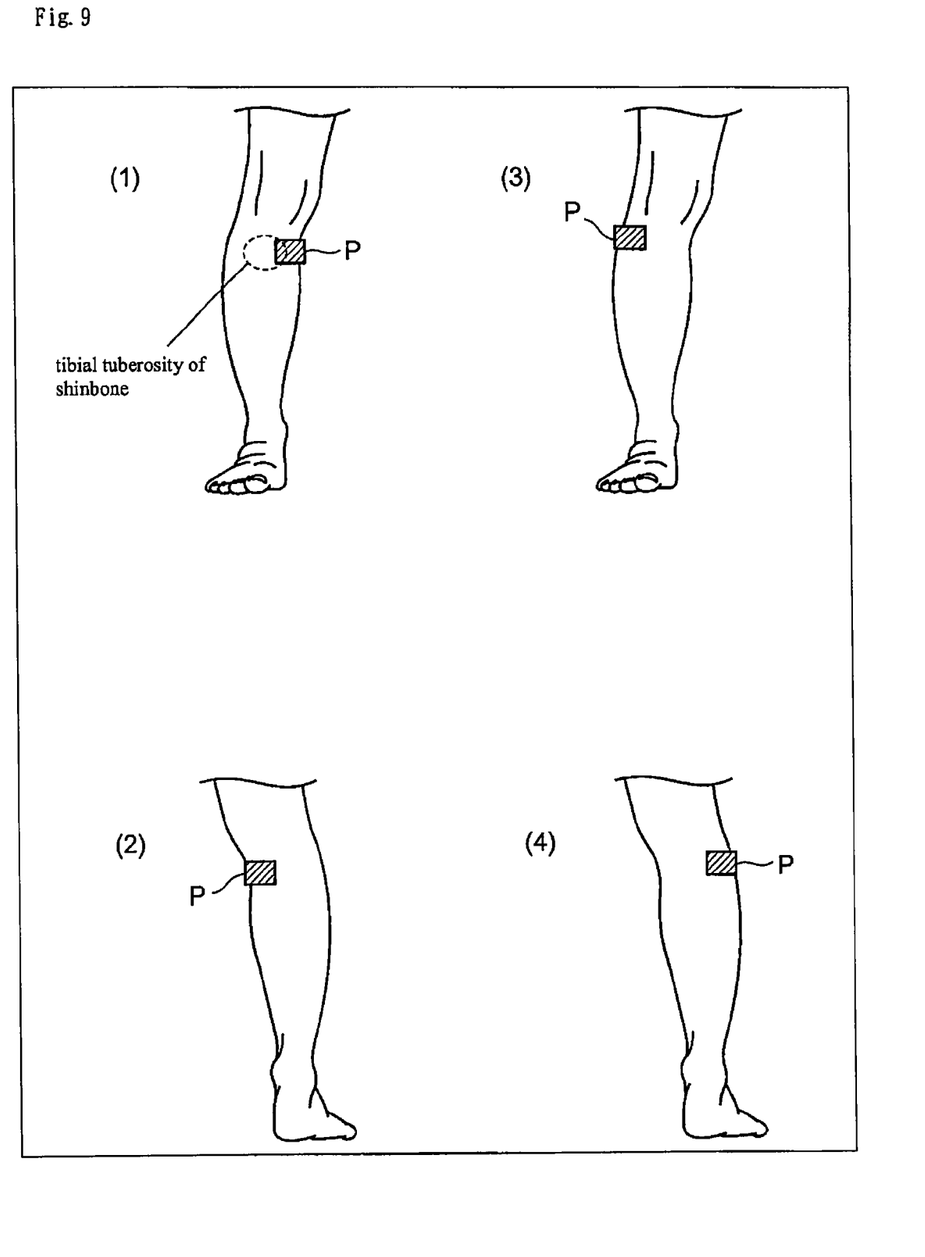
FIG. 9 is a schematic explanatory drawing of a leg for showing a contact portion of the projection of the knee support of the present invention.

An inner surface of the support main body 10 is provided with a projection 20 to be engaged with the shinbone below the knee from the inner side to the outer side direction along the pulling direction of a strap 30 to be described later, when wearing, at a region to be contacted with the inner side of the shinbone below the knee. In particular, as shown in FIG. 9(1), it is preferable to provide the same at an inner position by 0.5 to 3 cm from a center of a tibial tuberosity of the shinbone in terms of obtaining an effective engaging function with respect to the shinbone.

The form of the projection 20 may either be of square, circular, semi-circular, or the like; however, in terms of the engaging function with respect to the shinbone, a square is preferable. Moreover, its size is preferably 1.75 cm×4.5 cm and its thickness is about 0.8 cm. Furthermore, its material is not particularly limited; however, a soft material or an elastic material is more advantageous than a hard material in terms of not providing an uncomfortable pain to a region below the knee.

30 is a strap. As shown in the figure by an arrow, it is to be wound around and attached on the outer surface of the support main body 10 helically while being pulled in the direction opposite to the inner rotation direction of the knee joint.

Figure 10:
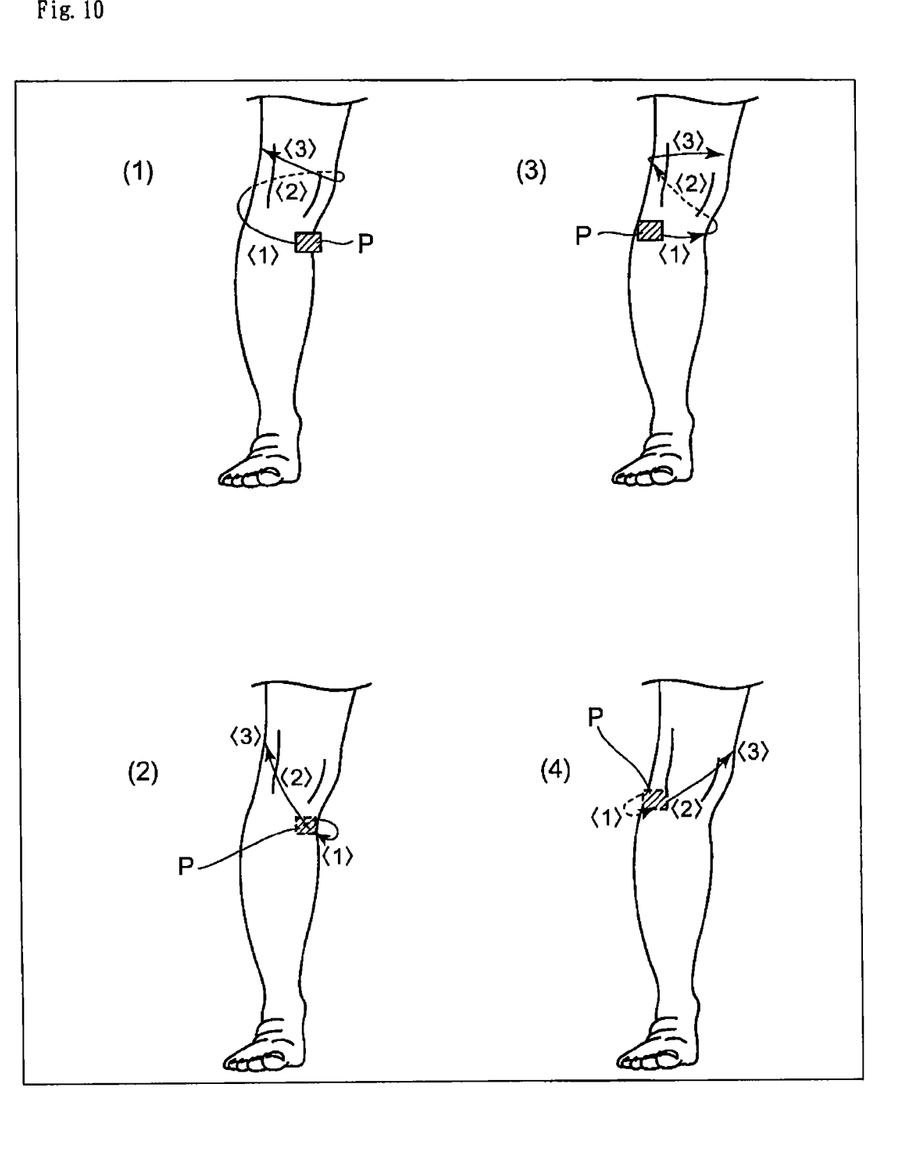
FIG. 10 is a schematic explanatory drawing of a leg for showing a winding route of the strap of the knee support of the present invention.

The specific winding route of the strap 30, as shown in the arrow in FIG. 10(1), is preferably as follows: <1> lower thigh: inner side region below knee→front surface region below knee→outer side region below knee→<2> knee back: obliquely upward on the knee back→<3> femoral region: inner side region above knee→front surface of femoral region. In this case, it presses the projection 20 at one end of the strap while it is wound around helically so that its other end is attached on the front surface of femoral region with a hook-and-loop fastener, and the like.

The strap 30 may be independent from the support main body 10. Alternatively, it may be integrated with the support main body 10 by preliminarily fixing its one end on the front surface of femoral region by sewing, and the like.

The size of the strap is not particularly limited. Its length is preferably about 30 to 60 cm, its width 2 to 6 cm, and its thickness 2 to 5 mm. Moreover, its material may be of any kind.

Figure 2:
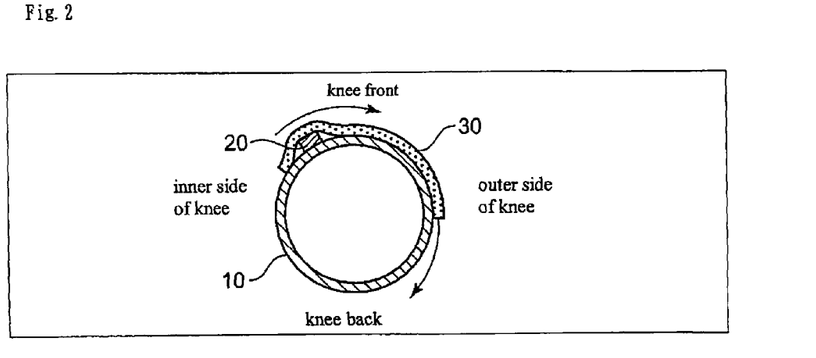
FIG. 2 is a schematic cross-sectional explanatory drawing for showing a second embodiment of a knee support of the present invention.

FIG. 2 is a schematic cross-sectional explanatory drawing for showing a support for restraining/correcting an inner rotation of the right leg according to a second embodiment of the present invention.

The second embodiment has the same component as that of the first embodiment shown in FIG. 1 except that the projection 20 is provided on the inner surface of the strap 30 instead of the support main body 10.

In the second embodiment, the projection 20 is contacted with the inner side of the shinbone via the support main body 10 when wearing.

Figure 3:
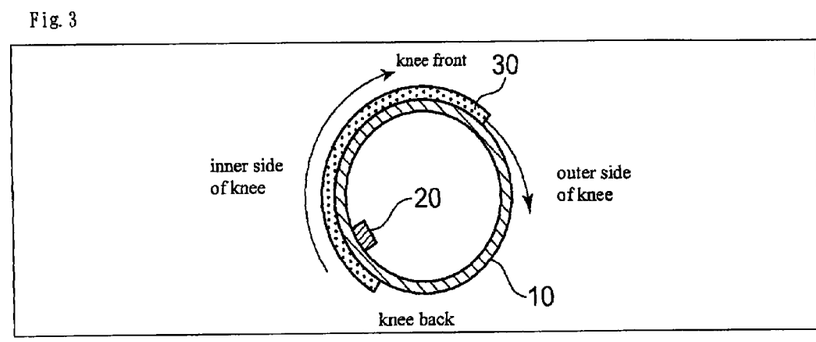
FIG. 3 is a schematic cross-sectional explanatory drawing for showing a third embodiment of a knee support of the present invention.

FIG. 3 is a schematic cross-sectional explanatory drawing for showing a support for restraining/correcting an inner rotation of the right leg according to a third embodiment of the present invention.

In FIG. 3, the inner surface of the support main body 10 is provided with a projection 20 to be engaged with the gastrocnemius muscle below the knee from the outer side to the inner side direction along the pulling direction of a strap 30, when wearing, at a portion to be contacted with the gastrocnemius muscle below the knee. In particular, as shown in FIG. 9(2), it is preferable to provide the same in the vicinity of a distal adhesion of the semimembranous muscle in terms of obtaining an effective engaging function with respect to the distal adhesion of the semimembranous muscle.

In this embodiment, as in the case of the first embodiment shown in FIG. 1, the strap 30 is wound around and attached on the outer surface of the support main body 10 helically while being pulled in the direction opposite to the inner rotation direction of the knee joint (arrow in the figure). The specific winding route, as shown in the arrow in FIG. 10(2), is preferably as follows: <1> lower thigh: inner side of lower thigh back→inner side of lower thigh front→<2> knee front: front surface of knee→obliquely upward on the front surface of knee→<3> femoral region: outer side of femoral region.

The other component is same as that of the first embodiment shown in FIG. 1.

Figure 4:
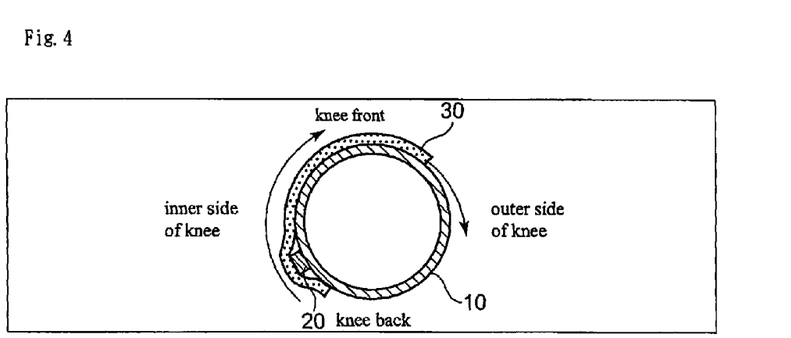
FIG. 4 is a schematic cross-sectional explanatory drawing for showing a fourth embodiment of a knee support of the present invention.

FIG. 4 is a schematic cross-sectional explanatory drawing for showing a support for restraining/correcting an inner rotation of the right leg according to a fourth embodiment of the present invention.

The fourth embodiment has the same component as that of the third embodiment shown in FIG. 3 except that the projection 20 is provided on the inner surface of the strap 30 instead of the support main body 10.

Figure 5:
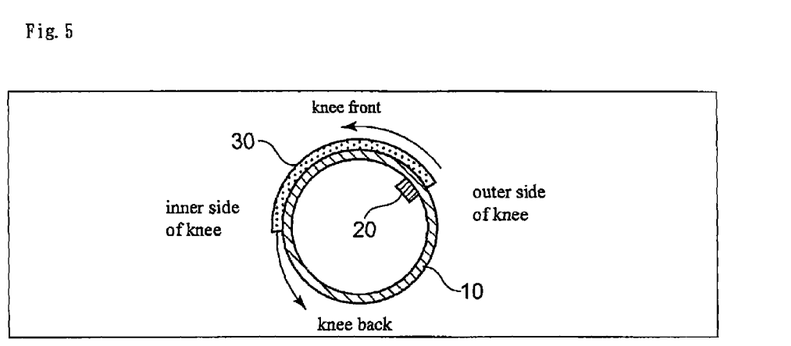
FIG. 5 is a schematic cross-sectional explanatory drawing for showing a fifth embodiment of a knee support of the present invention.

FIG. 5 is a schematic cross-sectional explanatory drawing for showing a support for restraining/correcting an outer rotation of the right leg according to a fifth embodiment of the present invention.

In FIG. 5, the inner surface of the support main body 10 is provided with a projection 20 to be engaged with the shinbone below the knee from the outer side to the inner side direction along the pulling direction of a strap 30, when wearing, at a portion to be contacted with the outer side of the shinbone below the knee. In particular, as shown in FIG. 9(3), it is preferable to provide the same at an outer position by 0.5 to 3 cm from a center of a tibial tuberosity of the shinbone in terms of obtaining an effective engaging function with respect to the shinbone.

In this embodiment, the strap 30 is wound around and attached on the outer surface of the support main body 10 helically while being pulled in the direction opposite to the outer rotation direction of the knee joint (arrow in the figure). The specific winding route, as shown in the arrow in FIG. 10(3), is preferably as follows: <1> lower thigh: outer side region below knee→front surface region below knee→inner side region below knee→<2> knee back: obliquely upward on the knee back→<3> femoral region: outer side region above knee→front surface of femoral region.

The other component is same as that of the first embodiment shown in FIG. 1.

Figure 6:
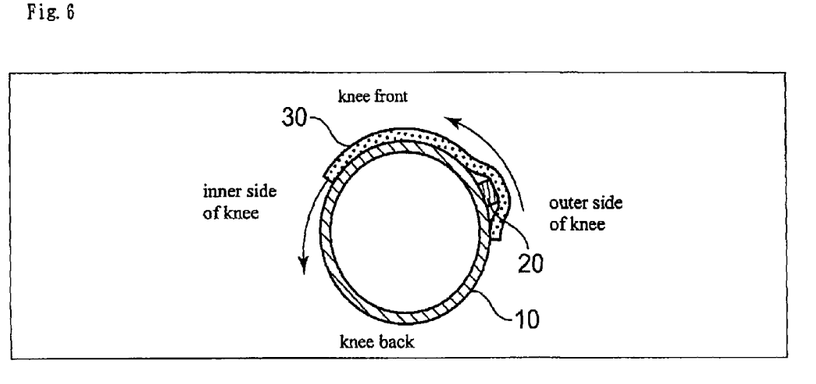
FIG. 6 is a schematic cross-sectional explanatory drawing for showing a sixth embodiment of a knee support of the present invention.

FIG. 6 is a schematic cross-sectional explanatory drawing for showing a support for restraining/correcting an outer rotation of the right leg according to a sixth embodiment of the present invention.

The sixth embodiment has the same component as that of the fifth embodiment shown in FIG. 5 except that the projection 20 is provided on the inner surface of the strap 30 instead of the support main body 10.

Figure 7:
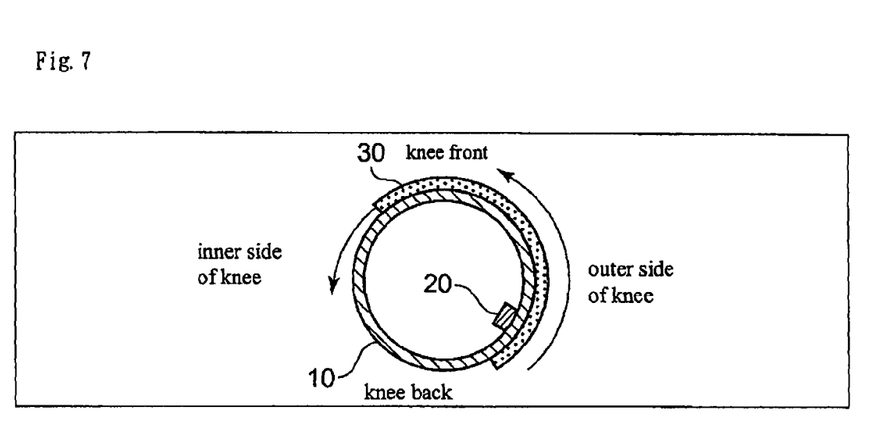
FIG. 7 is a schematic cross-sectional explanatory drawing for showing a seventh embodiment of a knee support of the present invention.

FIG. 7 is a schematic cross-sectional explanatory drawing for showing a support for restraining/correcting an outer rotation of the right leg according to a seventh embodiment of the present invention.

In FIG. 7, the inner surface of the support main body 10 is provided with a projection 20 to be engaged with the gastrocnemius muscle below the knee from the inner side to the outer side direction (arrow in the figure) along the pulling direction of a strap 30, when wearing, at a portion to be contacted with the gastrocnemius muscle below the knee. In particular, as shown in FIG. 9(4), is preferable to provide the same in the vicinity of a distal adhesion of the biceps femoris muscle in terms of obtaining an effective engaging function with respect to the distal adhesion of the biceps femoris muscle.

In this embodiment, as in the case of the fifth embodiment shown in FIG. 5, the strap 30 is wound around and attached on the outer surface of the support main body 10 helically while being pulled in the direction opposite to the outer rotation direction of the knee joint. The specific winding route, as shown in the arrow in FIG. 10(7), is preferably as follows: <1> lower thigh: outer side of thigh back→outer side of thigh front→<2> knee front: front surface of knee→obliquely upward on the front surface of knee→<3> femoral region: inner side of femoral region.

The other component is same as that of the first embodiment shown in FIG. 1.

Figure 8:
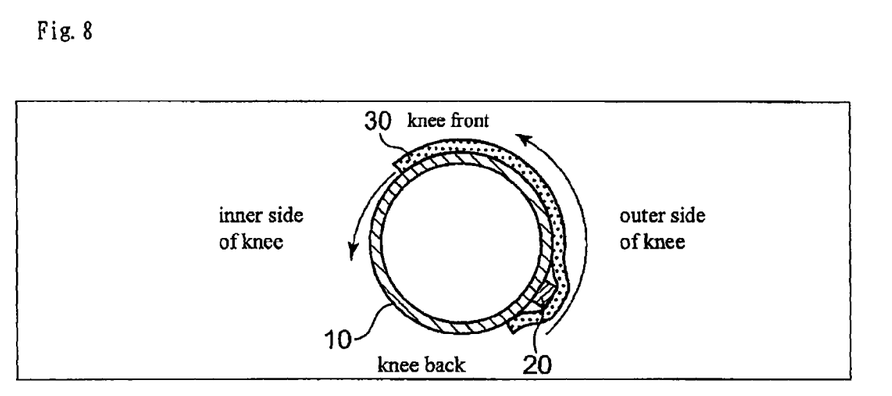
FIG. 8 is a schematic cross-sectional explanatory drawing for showing an eighth embodiment of a knee support of the present invention.

FIG. 8 is a schematic cross-sectional explanatory drawing for showing a support for restraining/correcting an inner rotation of the right leg according to an eighth embodiment of the present invention.

The eighth embodiment has the same component as that of the seventh embodiment shown in FIG. 7 except that the projection 20 is provided on the inner surface of the strap 30 instead of the support main body 10.

EXPLANATION OF REFERENCE

10: support main body
20: projection
30: strap
P: contact portion of projection

The invention claimed is:

1. A knee support being worn on a knee of a leg to provide support against an inner rotation of the knee joint, and comprising:
    a support main body covering the knee joint of the knee,
    one, and only one, strap attached on an outer surface of the support main body and helically wound around the support main body while successively passing from an inner side of the lower thigh of the leg to a knee back of the leg, with a distal end of the strap configured to be attached on the femoral region of the leg, wherein the strap is helically wound around the support main body so as to provide tension to the main body in a direction opposite to an inner rotation direction of the knee joint, and
    a projection provided on an inner surface of the support main body or an inner surface of the strap,
    wherein the knee support positioned on the knee such that the projection is engaged with the shinbone of the leg at an inner position by 0.5 to 3 cm from a center of a tibial tuberosity of the shinbone below the knee joint, and at a side of the shinbone such that the tension provided by the strap presses the projection against the shinbone, and
    wherein the knee support is positioned on the support main body or the strap such that the strap being helically wound around the support main body presses the projection onto the leg.

2. A knee support being worn on a knee of a leg to provide support against an inner rotation of the knee joint, and comprising:
    a support main body covering the knee joint of the knee,
    one, and only one, strap attached on an outer surface of the support main body and helically wound around the support main body while successively passing from an inner side of the lower thigh of the leg to a knee back of the leg, with a distal end of the strap configured to be attached on the femoral region of the leg, wherein the strap is helically wound around the support main body so as to provide tension to the main body in a direction opposite to an inner rotation direction of the knee joint, and
    a projection provided on an inner surface of the support main body or an inner surface of the strap,
    wherein the knee support positioned on the knee such that the projection is engaged with the gastrocnemius muscle of the leg at a location on the leg below the knee joint and in the vicinity of the distal adhesion of the gastrocnemius muscle, and at a side of the gastrocnemius muscle such that the tension provided by the strap presses the projection against the gastrocnemius muscle, and
    wherein the knee support is positioned on the support main body or the strap such that the strap being helically wound around the support main body presses the projection onto the leg.

3. A knee support being worn on a knee of a leg to provide support against an outer rotation of the knee joint, and comprising:
    a support main body covering the knee joint of the knee,
    one, and only one, strap attached on an outer surface of the support main body and helically wound around the support main body while successively passing from an outer side of the lower thigh of the leg to a knee back of the leg, with a distal end of the strap configured to be attached on the femoral region of the leg, wherein the strap is helically wound around the support main body so as to provide tension to the main body in a direction opposite to an outer rotation direction of the knee joint, and
    a projection provided on an inner surface of the support main body or an inner surface of the strap,
    wherein the knee support positioned on the knee such that the projection is engaged with the shinbone of the leg at an outer position by 0.5 to 3 cm from a center of a tibial tuberosity of the shinbone below the knee joint, and at a side of the shinbone such that the tension provided by the strap presses the projection against the shinbone, and wherein the knee support is positioned on the support main body or the strap such that the strap being helically wound around the support main body presses the projection onto the leg.

4. A knee support being worn on a knee of a leg to provide support against an outer rotation of the knee joint, and comprising:

a support main body covering the knee joint of the knee, one, and only one, strap attached on an outer surface of the support main body and helically wound around the support main body while successively passing from an outer side of the lower thigh of the leg to a knee back of the leg, with a distal end of the strap configured to be attached on the femoral region of the leg, wherein the strap is helically wound around the support main body so as to provide tension to the main body in a direction opposite to an outer rotation direction of the knee joint, and a projection provided on an inner surface of the support main body or an inner surface of the strap, wherein the knee support positioned on the knee such that the projection is engaged with a biceps femoris muscle of the leg at a location on the leg below the knee joint and in the vicinity of the distal adhesion of the biceps femoris muscle, and at a side of the biceps femoris muscle such that the tension provided by the strap presses the projection against the biceps femoris muscle, and wherein the knee support is positioned on the support main body or the strap such that the strap being helically wound around the support main body presses the projection onto the leg.

* * * * *